US006326180B1

(12) United States Patent
Wei et al.

(10) Patent No.: US 6,326,180 B1
(45) Date of Patent: Dec. 4, 2001

(54) ISOLATED HUMAN ENZYME, NUCLEIC ACID MOLECULES ENCODING HUMAN ENZYME, AND USES THEREOF

(75) Inventors: Ming-Hui Wei, Germantown; Chunhua Yan, Boyds; Valentina Di Francesco, Rockville; Ellen M. Beasley, Darnestown, all of MD (US)

(73) Assignee: PE Corporation (NY)

( * ) Notice: Subject to any disclaimer, the term of this patent is extended or adjusted under 35 U.S.C. 154(b) by 0 days.

(21) Appl. No.: 09/816,088

(22) Filed: Mar. 26, 2001

(51) Int. Cl.[7] ............................... C12N 9/02; C12N 1/20; C12N 15/00; C12Q 1/68; C07H 21/04

(52) U.S. Cl. .................... 435/189; 435/252.3; 435/320.1; 435/6; 536/23.2

(58) Field of Search ................................. 435/189, 252.3, 435/320.1, 6; 536/23.2

Primary Examiner—Ponnathapu Achutamurthy
Assistant Examiner—Yong Pak
(74) Attorney, Agent, or Firm—Celera Genomics; Robert A. Millman; Lin Sun-Hoffman

(57) ABSTRACT

The present invention provides amino acid sequences of peptides that are encoded by genes within the human genome, the enzyme peptides of the present invention. The present invention specifically provides isolated peptide and nucleic acid molecules, methods of identifying orthologs and paralogs of the enzyme peptides, and methods of identifying modulators of the enzyme peptides.

10 Claims, 10 Drawing Sheets

```
   1 TGGAGGAGCC AGCGGAAGGA CGGTGTGCGG GCCGGCCAGC CCTGGACGAA
  51 AGAAGAGGGC CCCTCCAGGC CAGTCTGGGC ACCCTGGGAT AGCGGCTGCA
 101 GCCAGGCATG GCCGACTCTG CACAGGCCCA GAAGCTGGTG TACCTGGTCA
 151 CAGGGGGCTG TGGCTTCCTG GGAGAGCACG TGGTGCGAAT GCTGCTGCAG
 201 CGGGAGCCCC GGCTCGGGGA GCTGCGGGTC TTTGACCAAC ACCTGGGTCC
 251 CTGGCTGGAG GAGCTGAAGA CAGGTACCCG GAACGTGATC GAGGCTTGTG
 301 TGCAGACCGG AACACGGTTC CTGGTCTACA CCAGCAGCAT GGAAGTTGTG
 351 GGGCCTAACA CCAAAGGTCA CCCCTTCTAC AGGGGCAACG AAGACACCCC
 401 ATACGAAGCA GTGCACAGGC ACCCCTATCC TTGCAGCAAG GCCCTGGCCG
 451 AGTGGCTGGT CCTGGAGGCC AACGGGAGGA AGGTCCGTGG GGGGCTGCCC
 501 CTGGTGACGT GTGCCCTTCG TCCCACGGGC ATCTACGGTG AAGGCCACCA
 551 GATCATGAGG GACTTCTACC GCCAGGGCCT GCGCCTGGGA GGTTGGCTCT
 601 TCCGGGCCAT CCCGGCCTCT GTGGAGCATG GCCGGGTCTA TGTGGGCAAT
 651 GTTGCCTGGA TGCACGTGCT GGCAGCCCGG GAGCTGGAGC AGCGGGCAGC
 701 CCTGATGGGC GGCCAGGTAT ACTTCTGCTA CGATGGATCA CCCTACAGGA
 751 GCTACGAGGA TTTCAACATG GAGTTCCTGG GCCCCTGCGG ACTGCGGCTG
 801 GTGGGCGCCC GCCCATTGCT GCCCTACTGG CTGCTGGTGT TCCTGGCTGC
 851 CCTCAATGCC CTGCTGCAGT GGCTGCTGCG GCCACTGGTG CTCTACGCAC
 901 CCCTGCTGAA CCCCTACACG CTGGCCGTGG CCAACACCAC CTTCACCGTC
 951 AGCACCGACA AGGCTCAGCG CCATTTCGGC TATGAGCCCC TGTTCTCGTG
1001 GGAGGATAGC CGGACCCGCA CCATTCTCTG GGTACAGGCC GCTACGGGTT
1051 CAGCCCAGTG ACGGTGGGGC TGGGGCCTGG AGGCCCAGAT ACAGCACATC
1101 CACCCAGGTC CCGAGCCCTC ACACCCTGGA CGGGAAGGGA CAGCTGCATT
1151 CCAGAGCAGG AGGCAGGGCT CTGGGGCCAG AATGGCTGTC CTTGTCGTAG
1201 AGCCCTCCAC ATTTTCTTTT TCTTTTTTGA GACAGGGTCT TGCTCTGTCA
1251 CCCAGACTGG AGTGCAGTGG TGTGATCATA GCTCACTGCA CCCTCAACCT
1301 CCTGGGTTCA AGCAATCCTC CTGCCTCAGC CTCCTGAACA GCTGGGACCA
1351 CAGGTGCACG CCACCATACC TGGCTTTTTT TTGTTGCTTT TAGAGACAGG
1401 GTCTCACTAT ATTGCTCAAG GCTGGACTTG AACTCCTGGG CTCAAGTGAT
1451 CTTCCCACGT GGGCCTCCCA AAACGCTGGA ACTACAAGTG TGAGCCACCG
1501 CGCCTGGCCC ACCGCCTCTC CACATTTTCA ATCCAGGAGC CTTGAGTCTG
1551 TGGCTGTGTC CTGACACCTC CAGAGTTCTG AGGGCCGTCA GGACACGGGA
1601 GGGTTTGGGG ACAGAGTGTC CTTCCTCTGT CCTATCATCA CCAGTCCTGA
1651 TGGCCGCTTG GTGAGTGTCT GGTGCCCTGG TGGCTTGCCC CAGCTCTCTT
1701 GTGGCTTTCT GAGCAGGAAG CGAGCACTAG GCTCCACAGG CTTACGCTGT
1751 GTCTCCTGCC AGCCACACAG CGACCCATCG GTGCAGAGTG CAGACGCGGG
1801 TGTGGTTCCT CCAGCCCACC TCAGTCCCTC TTTGGGAGGT GATGTTCCCA
1851 TTGTTTTTCA AAGGCCTCAC CTTCAACTGT TCTGTTTTAG AATTCCCCTC
1901 TGGAGGGCTA TGGCCTCCCT ATGGTTTCAC TTCCCACCTA CTTCTACCTA
1951 AGTTCCTTCC CAGCACATCG CCAGCCCTGG GCCTGGGGAT GTCCCCAATG
2001 CTGTACCTGG CTGACCCCGG ATTAAAAGCC TCATCCACGA AAAAAAAAAA
2051 AAAAAAAAAA AAAAAAAAAA A
```

(SEQ ID NO: 1)

FEATURES:
5'UTR:      1-107
Start Codon: 108
Stop Codon: 1059
3'UTR:      1062

```
   1 TGGAGGAGCC AGCGGAAGGA CGGTGTGCGG GCCGGCCAGC CCTGGACGAA
  51 AGAAGAGGGC CCCTCCAGGC CAGTCTGGGC ACCCTGGGAT AGCGGCTGCA
 101 GCCAGGCATG GCCGACTCTG CACAGGCCCA GAAGCTGGTG TACCTGGTCA
 151 CAGGGGGCTG TGGCTTCCTG GGAGAGCACG TGGTGCGAAT GCTGCTGCAG
 201 CGGGAGCCCC GGCTCGGGGA GCTGCGGGTC TTTGACCAAC ACCTGGGTCC
 251 CTGGCTGGAG GAGCTGAAGA CAGGTACCCG GAACGTGATC GAGGCTTGTG
 301 TGCAGACCGG AACACGGTTC CTGGTCTACA CCAGCAGCAT GGAAGTTGTG
 351 GGGCCTAACA CCAAAGGTCA CCCCTTCTAC AGGGGCAACG AAGACACCCC
 401 ATACGAAGCA GTGCACAGGC ACCCCTATCC TTGCAGCAAG GCCCTGGCCG
 451 AGTGGCTGGT CCTGGAGGCC AACGGGAGGA AGGTCCGTGG GGGGCTGCCC
 501 CTGGTGACGT GTGCCCTTCG TCCCACGGGC ATCTACGGTG AAGGCCACCA
 551 GATCATGAGG GACTTCTACC GCCAGGGCCT GCGCCTGGGA GGTTGGCTCT
 601 TCCGGGCCAT CCCGGCCTCT GTGGAGCATG GCCGGGTCTA TGTGGGCAAT
 651 GTTGCCTGGA TGCACGTGCT GGCAGCCCGG GAGCTGGAGC AGCGGGCAGC
 701 CCTGATGGGC GGCCAGGTAT ACTTCTGCTA CGATGGATCA CCCTACAGGA
 751 GCTACGAGGA TTTCAACATG GAGTTCCTGG GCCCCTGCGG ACTGCGGCTG
 801 GTGGGCGCCC GCCCATTGCT GCCCTACTGG CTGCTGGTGT TCCTGGCTGC
 851 CCTCAATGCC CTGCTGCAGT GGCTGCTGCG GCCACTGGTG CTCTACGCAC
 901 CCCTGCTGAA CCCCTACACG CTGGCCGTGG CCAACACCAC CTTCACCGTC
 951 AGCACCGACA AGGCTCAGCG CCATTTCGGC TATGAGCCCC TGTTCTCGTG
1001 GGAGGATAGC CGGACCCGCA CCATTCTCTG GGTACAGGCC GCTACGGGTT
1051 CAGCCCAGTG ACGGTGGGGC TGGGGCCTGG AGGCCAGAT ACAGCACATC
1101 CACCCAGGTC CCGAGCCCTC ACACCCTGGA CGGGAAGGGA CAGCTGCATT
1151 CCAGAGCAGG AGGCAGGGCT CTGGGGCCAG AATGGCTGTC CTTGTCGTAG
1201 AGCCCTCCAC ATTTTCTTTT TCTTTTTTGA GACAGGGTCT TGCTCTGTCA
1251 CCCAGACTGG AGTGCAGTGG TGTGATCATA GCTCACTGCA CCCTCAACCT
1301 CCTGGGTTCA AGCAATCCTC CTGCCTCAGC CTCCTGAACA GCTGGGACCA
1351 CAGGTGCACG CCACCATACC TGGCTTTTTT TTGTTGCTTT TAGAGACAGG
1401 GTCTCACTAT ATTGCTCAAG GCTGGACTTG AACTCCTGGG CTCAAGTGAT
1451 CTTCCCACGT GGGCCTCCCA AAACGCTGGA ACTACAAGTG TGAGCCACCG
1501 CGCCTGGCCC ACCGCCTCTC ACATTTTTCA ATCCAGGAGC CTTGAGTCTG
1551 TGGCTGTGTC CTGACACCTC CAGAGTTCTG AGGGCCGTCA GGACACGGGA
1601 GGGTTTGGGG ACAGAGTGTC CTTCCTCTGT CCTATCATCA CCAGTCCTGA
1651 TGGCCGCTTG GTGAGTGTCT GGTGCCCTGG TGGCTTGCCC CAGCTCTCTT
1701 GTGGCTTTCT GAGCAGGAAG CGAGCACTAG GCTCCACAGG CTTACGCTGT
1751 GTCTCCTGCC AGCCACACAG CGACCCATCG GTGCAGAGTG CAGACGCGGG
1801 TGTGGTTCCT CCAGCCCACC TCAGTCCCTC TTTGGGAGGT GATGTTCCCA
1851 TTGTTTTTCA AAGGCCTCAC CTTCAACTGT TCTGTTTTAG AATTCCCCTC
1901 TGGAGGGCTA TGGCCTCCCT ATGGTTTCAC TTCCCACCTA CTTCTACCTA
1951 AGTTCCTTCC CAGCACATCG CCAGCCCTGG GCCTGGGGAT GTCCCCAATG
2001 CTGTACCTGG CTGACCCCGG ATTAAAAGCC TCATCCACGA AAAAAAAAA
2051 AAAAAAAAAA AAAAAAAAA A
(SEQ ID NO: 1)
```

FEATURES:
5'UTR: 1-107
Start Codon: 108
Stop Codon: 1059
3'UTR: 1062

FIG.1A

```
HOMOLOGOUS PROTEINS:
Top 10 BLAST Hits:
CRA|335001098696094 /altid=gi|11545403 /def=gb|AAG37824.1|AF277...    638  0.0
CRA|335001098696092 /altid=gi|11545401 /def=gb|AAG37823.1|AF277...    562  e-159
CRA|18000005106837  /altid=gi|2563999  /def=dbj|BAA22931.1| (AB00...  484  e-136
CRA|18000005043125  /altid=gi|9629084  /def=ref|NP_044103.1| MC15...  269  3e-71
CRA|89000000192042  /altid=gi|9634716  /def=ref|NP_039008.1| ORF ...  257  2e-67
CRA|18000004899504  /altid=gi|540666   /def=pir||S41971 3beta-hydr... 240  1e-62
CRA|335001098644340 /altid=gi|11251676 /def=pir||T37430 hydroyx...    213  2e-54
CRA|18000004942649  /altid=gi|112779   /def=sp|P26670|3BHS_VACCV 3... 212  4e-54
CRA|18000004942648  /altid=gi|9791111  /def=ref|NP_063838.1| A44L...  211  9e-54
CRA|73000005493670  /altid=gi|9634564  /def=ref|NP_038102.1| TA55...  211  9e-54

EST:
gi|11283574 /dataset=dbest /taxon=96...                              1283  0.0
gi|11643588 /dataset=dbest /taxon=96...                              1116  0.0
gi|13134586 /dataset=dbest /taxon=960...                              527  e-147
gi|9334685  /dataset=dbest /taxon=960...                              462  e-128

EXPRESSION INFORMATION FOR MODULATORY USE:
gi|11283574 brain
gi|11643588 kidney
gi|13134586 colon
gi|9334685 uterus
```

FIG. 1B

```
  1 MADSAQAQKL VYLVTGGCGF LGEHVVRMLL QREPRLGELR VFDQHLGPWL
 51 EELKTGTRNV IEACVQTGTR FLVYTSSMEV VGPNTKGHPF YRGNEDTPYE
101 AVHRHPYPCS KALAEWLVLE ANGRKVRGGL PLVTCALRPT GIYGEGHQIM
151 RDFYRQGLRL GGWLFRAIPA SVEHGRVYVG NVAWMHVLAA RELEQRAALM
201 GGQVYFCYDG SPYRSYEDFN MEFLGPCGLR LVGARPLLPY WLLVFLAALN
251 ALLQWLLRPL VLYAPLLNPY TLAVANTTFT VSTDKAQRHF GYEPLFSWED
301 SRTRTILWVQ AATGSAQ
(SEQ ID NO: 2)
```

FEATURES:
Functional domains and key regions:
[1] PDOC00001 PS00001 ASN_GLYCOSYLATION
N-glycosylation site 276-279 NTTF

---

[2] PDOC00005 PS00005 PKC_PHOSPHO_SITE
Protein kinase C phosphorylation site 283-285 TDK

---

[3] PDOC00006 PS00006 CK2_PHOSPHO_SITE
Casein kinase II phosphorylation site

Number of matches: 4
    1      76-79 SSME 2     97-100 TPYE 3   215-218 SYED 4   297-300 SWED

---

[4] PDOC00007 PS00007 TYR_PHOSPHO_SITE
Tyrosine kinase phosphorylation site 92-99 RGNEDTPY

---

[5] PDOC00008 PS00008 MYRISTYL
N-myristoylation site 157-162 GLRLGG

---

[6] PDOC00009 PS00009 AMIDATION
Amidation site 122-125 NGRK

---

[7] PDOC00029 PS00029 LEUCINE_ZIPPER
Leucine zipper pattern 246-267 LAALNALLQWLLRPLVLYAPLL

FIG.2A

Membrane spanning structure and domains:
```
Helix  Begin  End   Score  Certainty
  1      6    26    0.633  Putative
  2    237   257    1.571  Certain
  3    260   280    0.819  Putative
```

BLAST Alignment to Top Hit:
>CRA|335001098696094 /altid=gi|11545403
    /def=gb|AAG37824.1|AF277719_1 (AF277719) 3
    beta-hydroxy-delta 5-C27-steroid oxidoreductase [Homo
    sapiens] /org=Homo sapiens /taxon=9606 /dataset=nraa
    /length=369
    Length = 369

Score = 638 bits (1627), Expect = 0.0
Identities = 315/369 (85%), Positives = 316/369 (85%), Gaps = 52/369 (14%)

```
Query:   1  MADSAQAQKLVYLVTGGCGFLGEHVVRMLLQREPRLGELRVFDQHLGPWLEELKTG----  56
            MADSAQAQKLVYLVTGGCGFLGEHVVRMLLQREPRLGELRVFDQHLGPWLEELKTG
Sbjct:   1  MADSAQAQKLVYLVTGGCGFLGEHVVRMLLQREPRLGELRVFDQHLGPWLEELKTGPVRV  60

Query:  57  ---------------------------------------TRNVIEACVQTG  68
                                                   TRNVIEACVQTG
Sbjct:  61  TAIQGDVTQAHEVAAAVAGAHVVIHTAGLVDVFGRASPKTIHEVNVQGTRNVIEACVQTG 120

Query:  69  TRFLVYTSSMEVVGPNTKGHPFYRGNEDTPYEAVHRHPYPCSKALAEWLVLEANGRKVRG 128
            TRFLVYTSSMEVVGPNTKGHPFYRGNEDTPYEAVHRHPYPCSKALAEWLVLEANGRKVRG
Sbjct: 121  TRFLVYTSSMEVVGPNTKGHPFYRGNEDTPYEAVHRHPYPCSKALAEWLVLEANGRKVRG 180

Query: 129  GLPLVTCALRPTGIYGEGHQIMRDFYRQGLRLGGWLFRAIPASVEHGRVYVGNVAWMHVL 188
            GLPLVTCALRPTGIYGEGHQIMRDFYRQGLRLGGWLFRAIPASVEHGRVYVGNVAWMHVL
Sbjct: 181  GLPLVTCALRPTGIYGEGHQIMRDFYRQGLRLGGWLFRAIPASVEHGRVYVGNVAWMHVL 240

Query: 189  AARELEQRAALMGGQVYFCYDGSPYRSYEDFNMEFLGPCGLRLVGARPLLPYWLLVFLAA 248
            AARELEQRAALMGGQVYFCYDGSP+RSYEDFNMEFLGPCGLRLVGARPLLPYWLLVFLAA
Sbjct: 241  AARELEQRAALMGGQVYFCYDGSPHRSYEDFNMEFLGPCGLRLVGARPLLPYWLLVFLAA 300

Query: 249  LNALLQWLLRPLVLYAPLLNPYTLAVANTTFTVSTDKAQRHFGYEPLFSWEDSRTRTILW 308
            LNALLQWLLRPLVLYAPLLNPYTLAVAN TFTVSTDKAQRHFGYEPLFSWEDSRTRTILW
Sbjct: 301  LNALLQWLLRPLVLYAPLLNPYTLAVANATFTVSTDKAQRHFGYEPLFSWEDSRTRTILW 360

Query: 309  VQAATGSAQ  317
            VQAATGSAQ
Sbjct: 361  VQAATGSAQ  369 (SEQ ID NO: 4)
```

Hmmer search results (Pfam):
Scores for sequence family classification (score includes all domains):
```
Model    Description                                      Score      E-value   N
-------  -----------                                      -----      -------   ---
PF01073  3-beta hydroxysteroid dehydrogenase/isomeras     558.2      5.5e-164   2
```

FIG. 2B

```
PF01370  NAD dependent epimerase/dehydratase family    13.3    0.005   1
PF00438  S-adenosylmethionine synthetase                1.8    0.78    1

Parsed for domains:
Model    Domain  seq-f seq-t    hmm-f hmm-t     score  E-value
-------  ------  ----- -----    ----- -----     -----  -------
PF01370   1/1      12    31 ..     1    20 [.    13.3    0.005
PF01073   1/2       1    52 [.     1    53 [.    69.6  3.9e-18
PF00438   1/1     289   299 ..   365   376 .]     1.8    0.78
PF01073   2/2      55   313 ..   159   425 .]   489.6  2.4e-143
```

FIG.2C

```
   1 ATTTGCATTA GCCGGTGGCA GCCAACAGGT GCCTGTTTTG GAGAGAGGTC
  51 CAGGGAGGAG AGATGAGCAG GGTGCCGTTG GTGACATGGC CAGTCATTTC
 101 AGGAGCTGCC CCAACCCCAG ACTTGCCCCA GCAGTCCGGG ACCCCACTGT
 151 GACCAGGCAG ATGCTCGAAG GAGTCAGTGG CTCTCTTACC CAGTGCAGAT
 201 TTCCCTGGAG TTCCCTGCGG GTGACTTAGA ATGGCCACCA GAGGCTTAGG
 251 ATGCTGCCCC AAAGAGGGAG GGCTCCTGGA AGCAGAGTCG AGAGAGTCAG
 301 TGCCGGGTTA GCGGGAGCTG GAGGCAGAGC TGCAGCTCCA GGCCTGGTGG
 351 GCGTGGACCT GGGGTGCTGG CTGGCAGGCG TGCTCAGGGG CAGGAAGTGG
 401 GGGACTCTTC CCTGACCATC GCATCTCACC CTGGCAGATG GTGGCCGACA
 451 TGCGGGAGAA GCGCTACGTG CAGGAGGGCA TTGGCAGCAG CTACCTGTTC
 501 CGGGTGGACC ACGACACCAT CATCGATGCC ACCAAGTGTG GCAACCTGGC
 551 CAGATTCATC AACCACTGCT GCACGGTGCG CCAGGGGCCA GCCGGGGCAG
 601 GAGTTGGGGG TCGGTGGGGG TGGCCACGGC TCACACGCCC TTCCATCCGC
 651 AGCCTAACTG CTACGCCAAG GTCATCACCA TCGAGTCCCA GAAGAAGATC
 701 GTGATCTACT CCAAGCAGCC CATTGGCGTG GACGAGGAGA TCACCTACGA
 751 CTACAAGTTC CCACTGGAAG ACAACAAGAT CCCGTGTCTG TGTGGCACAG
 801 AGAGCTGCCG GGGCTCCCTA AACTGAGGTG GGGCAGGATG GGTGCCCACA
 851 CCCCTATTTA TTCCCCCTGG TGCCCTGAGC TCCCAGCACC CCCCCAGCCT
 901 TAGTGGGCTC AGCAGGGCCC ACATGCCCCC ATCTCCAAGC GTGGGGTTGG
 951 GGGCCCCAAG CCCAGCGAGG GAGCCTCAGT CCCTGGAGGC AGCTTCTGCC
1001 TCTCCTGTCG CCCCTGCCCA CCACCCCCTG ATTGTTTTTC TTTGCGGAGA
1051 AGAAGCTGTA AATGTTTTGT AGCAGCCAGC AGCTGTTTCC TGTGGAAACC
1101 TGGGGTGCCG GCCTGTACAG ATTCTGTCCT GGGGGGCTAC ACAGTCCTCT
1151 CGCTTTGTGT TAATGGGGAC TTCCCCTTAC GCCCTGCGTG TACCCCTCCC
1201 CAGTTTAGGG GTCTCTGGGG CAGTGGCCAT GTTCTCCCCC TGGGGGGGCT
1251 CTGCACCCCC AGTCCTGGGG ACTCCGTGCC TGGAACCCTG CCTCATCTGT
1301 TCCTGCCAGA CCCTGAGGGT CACCCTTCCA CCCTGGTGTC ACTCCCCGGC
1351 TCAGCCAGGC CAGGATGGCG GGGTGGGTCC CTTTTGCTGG GCTGGACTGT
1401 ACATATGTTA ATAGCGCAAA CCCGACGCCA CATTTTTATA ATTGTGATTA
1451 AACTTTATTG TACAAAAGTG TTTGGTCGGT GTATTTGGGC AGGAGCGAGG
1501 GGTTGGGGGT AGAGGGCACG GAGGGTTGTG CAAGTTGAAG AGAGGGAAAA
1551 GTGGGTACCT GAAGTGTGGG GCAGGTAAAG GGGCCTTCAG GCAAGAGCCC
1601 AGACCTGCAG AGACAGTCCG AGACTGTCTC GGACCCCCTG ACAGGCTGCA
1651 GCAGCCGCAC CCGCACCAGG AATACCCCAC CAGTGCCCGC CAGGGTGGTG
1701 CCAAGGTCAG GCCTCCCCTT CCTACAATCA CAGCTGCAGC TGGACCTCCG
1751 GCCTCCTGGG AAGCCCAGCA GGAGGGAAGG CCTGAGGTCA CACTGTGGGA
1801 TGAGGTCACC GCTGGCTCCA CCCACAGCCC CAGACCCCTT CAGCCCACTC
1851 TGCAAGTTCG AGCTTCATCC CCACCAAGTT CTCCGCTGGA CCCAGATGCC
1901 AGTGGAGCAC AGAGCGGCCG CCAGGGGGCG CCTTGGGGCA AGAGTGGTGG
1951 GGGTTGTGGC TGGGCGGGTC TCTGTTCCTG GAATGGGGCA GGAGGGAGAA
2001 GGAGGAGCCA GCGGAAGGAC GGTGTGCGGG CCGGCCAGCC CTGGACGAAA
2051 GAAGAGGGCC CCTCCAGGCC AGTCTGGGCA CCCTGGGATA GCGGCTGCAG
2101 GTAGGCAGAG GCGCTGCCAG TGCCCAGGTG GCCTTTCCCT CCATCCGGCC
2151 CTTCCCACCT TCCTATAACC TTCCCTCCAC CTCCCTCAAC TCCTGGCCTC
2201 CCCACCCTTT TACTGCCTTC AAATCTCTCT CCCTAAACCC TGACCCCTTC
2251 CTGCACCCCA AGCCCGCCCC TCTCTCCGTA ACTCAGCCAT CAGCAGGGGC
2301 AGACGGCAGG TGGCCTGGTT GCTGCAGCTC CCAGGATCAG CTCTGCCCTC
2351 CCGCCAAACG CCAGCCTCGT CACCGCTCCA GGGCACCTCC AGCAGTAACA
2401 GGTGGTTGCA GCAGGTGGCA GCCAGCCCCT GGATGAGCCA AGGTCTCTTC
2451 CCCAGCCAGG CATGGCCGAC TCTGCACAGG CCCAGAAGCT GGTGTACCTG
```

FIG.3A

```
2501 GTCACAGGGG GCTGTGGCTT CCTGGGAGAG CACGTGGTGC GAATGCTGCT
2551 GCAGCGGGAG CCCCGGCTCG GGGAGCTGCG GGTCTTTGAC CAACACCTGG
2601 GTCCCTGGCT GGAGGAGCTG AAGACAGGTT CTTGTTGGGG GAGCTTGTGG
2651 TGGAGAGGGT GTGGACGCTT CCCCAACCCT TCCCAAGCTG GGATCCCCAC
2701 CCCTGCAGTG GAACAGATGA TGCTGGTTTC TGTCCACATG GATGGGTCGA
2751 GTGAGTCACA TTGGGAACGT GACTCCAGGG TGGAAGATGA ACCCAGCCTC
2801 TGGCCTCTGG CCCCAGCTCT GACATGGCCT GTGTCCTCCA ACCCCGGCCA
2851 GGGCCTGTGA GGGTGACTGC CATCCAGGGG GACGTGACCC AGGCCCATGA
2901 GGTGGCAGCA GCTGTGGCCG GAGCCCATGT GGTCATCCAC ACGGCTGGGC
2951 TGGTAGACGT GTTTGGCAGG GCCAGTCCCA AGACCATCCA TGAGGTCAAC
3001 GTGCAGGGTG AGGAGCTCTG GACACTCCTG GCCATCTTGC CTGTTTGTTC
3051 CCCACTCTGT CTTTGGCCTT GACCTCCGGT GACTCCCCTG GGACAAGTTG
3101 TCCTATTGAC AGCCCTGCCC CCGCCTCCCC TGACCTGTCA TGGTTTTCCC
3151 TGGACCTGGG ATGGGGAGGA GGAAGATGCA GAGAGGGAAG AAGCTGCAGC
3201 TTGGATACGC CTCCTCCTCT GCCAGGTACC CGGAACGTGA TCGAGGCTTG
3251 TGTGCAGACC GGAACACGGT TCCTGGTCTA CACCAGCAGC ATGGAAGTTG
3301 TGGGGCCTAA CACCAAAGGT CACCCCTTCT ACAGGTGAGT GGCAGGCCCT
3351 CTTGTCCTCT AAGAGCCCAT TTCCCTCAGC ATTGAGTCTT CCTTCTCCTC
3401 CCACCAGGGG CAACGAAGAC ACCCCATACG AAGCAGTGCA CAGGCACCCC
3451 TATCCTTGCA GCAAGGCCCT GGCCGAGTGG CTGGTCCTGG AGGCCAACGG
3501 GAGGAAGGTG AGCCCAGAAA AAGGAGGCGC AGAGATGGGG CTCCTGCCCT
3551 GCACACCCCC TTACCCTGCC AGCCCAAGGA GGCCGGGGCC GAGAGCAAGC
3601 TGTCGGGTCC CAGGTCTCAG CAGTACCTGC CTTTGCCACC AGGTCCGTGG
3651 GGGGCTGCCC CTGGTGACGT GTGCCCTTCG TCCCACGGGC ATCTACGGTG
3701 AAGGCCACCA GATCATGAGG GACTTCTACC GCCAGGGCCT GCGCCTGGGA
3751 GGTTGGCTCT TCCGGGCCAT CCCGGCCTCT GTGGAGCATG GCCGGGTCTA
3801 TGTGGGTGAG GACTGGGCTA GGCAGGGGA GGCTGAGAAT ATGGCAGGAG
3851 GACTTGCTCT AGAAGGGGGC AGGACCCACA TGGCCCTGGG AGAGAAGTGT
3901 GGACTCTGGC TAGAAAAATA TGGTCTATAC ATGGGCCAAG GTAGACTGTG
3951 ATTATGTCTC CACAGCCTGC AGAGAATACA GGATCCATGC AAGTTGGGAC
4001 ATTAAAAAGT GTATCATAGG CTACAGAGAA GATTGCAGCT ATGGGAGCAG
4051 CCATTCCCCA GGAGAGGAGA GGAGAGGGAC AGTGTGTACA CAGCACTAAA
4101 AGGGCTGGGT TCAGTGGCTC GCATCTATAA TCCCAGCACT TTAGGAGGCT
4151 GAGGCGGGAG GATGGCCTGA GCCCAGGAGT TGGAGGCTGC AGTGAGCTAT
4201 GACCGCACCA CTGCACTCCA GCCTGGATGA CAGAGACAGA CCCTGTCTCT
4251 AAAACTTTTT TTAAAGGAAG TAGCATCTAC ACAGGGAATA AGGTCACCTG
4301 CCACTCCATC CTGCAGTCCC CAAGCCTCTC AGGGCCCACC ACGCAGGTCC
4351 TGGTTTCTCT ATCCTCTCCC CAGGTTCTTT GCAGATGCAG GCTGGCCCAG
4401 GAGAGCAAGT GACTACCAGG GCGAGGGAGA AGGCAGCCTT TCCCAGGCTG
4451 CTGTGGGGAT GTGGGCGGCA ACTACCTGGG CCCAAAGAGG GGGTGGCCCA
4501 GGAGAGCAGC CTCGATGTGG TGTTGCAAGG GCACTCAGGG GTGTGTCCGC
4551 CTCTCTTCCG CCACCGGCAG GCAATGTTGC CTGGATGCAC GTGCTGGCAG
4601 CCCGGGAGCT GGAGCAGCGG GCAGCCCTGA TGGGCGGCCA GGTATACTTC
4651 TGCTACGATG GATCACCCTA CAGGAGCTAC GAGGATTTCA ACATGGAGTT
4701 CCTGGGCCCC TGCGGACTGC GGCTGGTGGG CGCCCGCCCA TTGCTGCCCT
4751 ACTGGCTGCT GGTGTTCCTG GCTGCCCTCA ATGCCCTGCT GCAGTGGCTG
4801 CTGCGGCCAC TGGTGCTCTA CGCACCCCTG CTGAACCCCT ACACGCTGGC
4851 CGTGGCCAAC ACCACCTTCA CCGTCAGCAC CGACAAGGCT CAGCGCCATT
4901 TCGGCTATGA GCCCCTGTTC TCGTGGGAGG ATAGCCGGAC CCGCACCATT
4951 CTCTGGGTAC AGGCCGCTAC GGGTTCAGCC CAGTGACGGT GGGGCTGGGG
```

FIG.3B

```
5001 CCTGGAGGCC CAGATACAGC ACATCCACCC AGGTCCCGAG CCCTCACACC
5051 CTGGACGGGA AGGGACAGCT GCATTCCAGA GCAGGAGGCA GGGCTTCTGG
5101 GGCCAGAATG GCTGTCCTTG TCGTAGAGCC CTCCACATTT TCTTTTTCTT
5151 TTTTGAGACA GGGTCTTGCT CTGTCACCCA GACTGGAGTG CAGTGGTGTG
5201 ATCATAGCTC ACTGCACCCT CAACCTCCTG GGTTCAAGCA ATCCTCCTGC
5251 CTCAGCCTCC TTGAACAGCT GGGACCACAG GTGCACGCCA CCACACCTGG
5301 CTTTTTTTTG TTGTTTTTAG AGACAGGGTC TCACTATATT GCTCAGGCTG
5351 GTCTTGAACT CCTGGGCTCA AGTGATCTTC CCACGTGGGC CTCCCAAAAC
5401 GCTGGAACTA CAAGTGTGAG CCACCGCGCC TGGCCCAAGC CCTCCACATT
5451 TTCAATCCAG GAGCCTTGAG TCTGTGTTGT GTCCTGACAC CTCCAAGTTC
5501 TAGGGCCGTC AGGACACGGG AGGGTTTGGG GACAGAGTGT CCTTCCTCTG
5551 TCCTCTCATC CCAGTCCTGA TGGCCGCTTG GTGAGTGTCT GGTGCCCTGG
5601 TGGCCTGCCC CAGCTCTCTT CTGGCTTTCT GAGCAGGAAG CGAGCAGAGG
5651 CTCCACAGGC TTACGCTGCT CTCCTGACAG CCACACGCGA CCCTCGGTGC
5701 AGAGTGCAGA GGCGGCTCTG GTTCCTCCAG CCACCTCAGT CCCTCTTTGG
5751 GAGGTGATGT TCCCATTGTT TTTCAAAGGC CTCACCTTCA ACTGTCTGTC
5801 TTAGAATTCC CCTCTGGAGG GCTATGGCCT CCCTATGCTT TCACTTCCCA
5851 CCTCTCTACC TAAGTTCCTT CCCAGCACAT CGCCAGCCCT GGGCCTGGGG
5901 ATGTCCCCAA TGCTGTACCT GGCTGACCCC GGATTAAAAG CCTCATCCAC
5951 GACCGTGTCC ATCTGTCTGT CCAGCTCTCC CTCCCATCCC CCCACCCCAT
6001 GTCCGCCTCC CCACGGCGCC CATCCCACGT GGGGACAGAA GGAAGTGAGC
6051 ACACGGCACA CCCGCTGTTG GATTGGTTGC TATTTCTCCC GTCCCACAGG
6101 GCCTGACCTG GCCCAGGGTG GGGTGGGGGG CTCTGGGGAC AGGACATGCA
6151 GGGAGGAAGG GGGGGGCAGG ATTTTCCTGT GTTTTATCCA TTTGCAAGTT
6201 GGTCACCAAT AGAAATGGGA CTCTGAGGGC TAACAGAAAT GGGACTCTGA
6251 GGGCTAACAG GAGAGGGCGG CCTGGCTCTG GCCCCAGCC AGGCCCCAGG
6301 AGTCCTGTCC CCTCTGAGAA GGGGAGGGAG AGAGCTCTAG AAACCAACGG
6351 AGAAACAGAG AAGGGGGCAG GGGCTCATGT CAGCAAACAC GGCTACATCA
6401 CGTGACACGC CAGTGACACA GAAACACACG CCAACGCACA CGGCTGCACA
6451 GCGGGCAGGG GCGGTTAGGG GAAAGGGAGC CGGGGCCACC CATCTTGTCC
6501 TCTGCAGGGC GGGCTGGGGG GCAGGGTGAA TGCATAGAAC ACATCATGTG
6551 TACACGCTCA GGGCGTGGCA AGAGCGTGCG TCGACCCACG GGTACATGGG
6601 ATGGACACGC AGTGTGCTTC ATGAGGGGTG GGAACAGGGA GGAGGGGGAA
6651 GAGGAAGCAC TGAGCCCTGG CCAGGCCCGG GACCACCCGC AGGGCACACG
6701 TGGGCACAT GTGGGCTCAA TGGTTGCAGG CGCCTGGGCA GGTAGCACAC
6751 ATTTGTCCAA GAACATGCAA AAGACACCAG CCTCCAGACA ACATGCCAGG
6801 ACGCACACAG ACAGCAGCCA ACAAGCAGGC ACATCATAGG ATGTGGAGGA
6851 CGCATAGAAA GGGCACAGCA GACCCTTAGA GATCCCCTGG TCCACCTGAG
6901 GCCCAGAGAT GGGCAGCTGT GGGCCCAATG CCACTCCAGG TGGGGGGAGT
6951 GGTGCCCCAG CCACGCTTCA ACCCTTCTCC TGTGGCCCCA AGGCCGTGGG
7001 ACTTCCGGAA ACACCTGGGC TGAATGGGGG TCCTGTCCAG GCGGCCGGAA
7051 GAGGGGACTG GGGGCTGGGG CCTGCTCTGA TGTCTCCCAA GCAGCCCGAG
7101 ATGGGAGCAG GAGGGCCGTG GCCAGACTTG GGGCAGACTT CCTGTCCTGC
7151 AGAGGGGCGT TCTGGGAAGG GACAGGCAGG CCCCAGCTC AGGACAGCCC
7201 ACCTGGGGTT ACGCACGTGG CCACACTGAC ACACACACAG GACAAGGGAG
7251 AGCTCGGCTG TCTGAGCTCG GGTAGAGGTG GAGGGGTACT GTGTTCTGGG
7301 A
         (SEQ ID NO: 3)
```

FIG.3C

FEATURES:
Start: 2462
Exon: 2462-2627
Intron: 2628-3225
Exon: 3226-3334
Intron: 3335-3407
Exon: 3408-3507
Intron: 3508-3642
Exon: 3643-3805
Intron: 3806-4570
Exon: 4571-4983
Stop 4984

SNPs:

| DNA Position | Major | Minor | Domain | Protein Position | Major | Minor |
|---|---|---|---|---|---|---|
| 1010 | A | G | Beyond ORF(5') | | | |
| 1151 | C | T | Beyond ORF(5') | | | |
| 4805 | G | A | Exon | 258 | R | Q |
| 6293 | G | A | Beyond ORF(3') | | | |

Context:

| DNA Position | |
|---|---|
| 1010 | TCCAAGCAGCCCATTGGCGTGGACGAGGAGATCACCTACGACTACAAGTTCCCACTGGAA<br>GACAACAAGATCCCGTGTCTGTGTGGCACAGAGAGCTGCCGGGGCTCCCTAAACTGAGGT<br>GGGGCAGGATGGGTGCCCACACCCCTATTTATTCCCCCTGGTGCCCTGAGCTCCCAGCAC<br>CCCCCCAGCCTTAGTGGGCTCAGCAGGGCCCACATGCCCCCATCTCCAAGCGTGGGGTTG<br>GGGGCCCCAAGCCCAGCGAGGGAGCCTCAGTCCCTGGAGGCAGCTTCTGCCTCTCCTGTC<br>[A,G]<br>CCCCTGCCCACCACCCCTGATTGTTTTTCTTTGCGGAGAAGAAGCTGTAAATGTTTTGT<br>AGCAGCCAGCAGCTGTTTCCTGTGGAAACCTGGGGTGCCGGCCTGTACAGATTCTGTCCT<br>GGGGGGCTACACAGTCCTCTCGCTTTGTGTTAATGGGGACTTCCCCTTACGCCCTGCGTG<br>TACCCCTCCCCAGTTTAGGGGTCTCTGGGGCAGTGGCCATGTTCTCCCCCTGGGGGGGCT<br>CTGCACCCCAGTCCTGGGGACTCCGTGCCTGGAACCCTGCCTCATCTGTTCCTGCCAGA |
| 1151 | CCCCTATTTATTCCCCCTGGTGCCCTGAGCTCCCAGCACCCCCCCAGCCTTAGTGGGCTC<br>AGCAGGGCCCACATGCCCCCATCTCCAAGCGTGGGGTTGGGGGCCCCAAGCCCAGCGAGG<br>GAGCCTCAGTCCCTGGAGGCAGCTTCTGCCTCTCCTGTCGCCCCTGCCCACCACCCCCTG<br>ATTGTTTTTCTTTGCGGAGAAGAAGCTGTAAATGTTTTGTAGCAGCCAGCAGCTGTTTCC<br>TGTGGAAACCTGGGGTGCCGGCCTGTACAGATTCTGTCCTGGGGGGCTACACAGTCCTCT<br>[C,T]<br>GCTTTGTGTTAATGGGGACTTCCCCTTACGCCCTGCGTGTACCCCTCCCCAGTTTAGGGG<br>TCTCTGGGGCAGTGGCCATGTTCTCCCCCTGGGGGGGCTCTGCACCCCAGTCCTGGGGA<br>CTCCGTGCCTGGAACCCTGCCTCATCTGTTCCTGCCAGACCCTGAGGGTCACCCTTCCAC |

FIG.3D

```
         CCTGGTGTCACTCCCCGGCTCAGCCAGGCCAGGATGGCGGGGTGGGTCCCTTTTGCTGGG
         CTGGACTGTACATATGTTAATAGCGCAAACCCGACGCCACATTTTTTATAATTGTGATTAA
4805     AGCAGCCTCGATGTGGTGTTGCAAGGGCACTCAGGGGTGTGTCCGCCTCTCTTCCGCCAC
         CGGCAGGCAATGTTGCCTGGATGCACGTGCTGGCAGCCCGGGAGCTGGAGCAGCGGGCAG
         CCCTGATGGGCGGCCAGGTATACTTCTGCTACGATGGATCACCCTACAGGAGCTACGAGG
         ATTTCAACATGGAGTTCCTGGGCCCCTGCGGACTGCGGCTGGTGGGCGCCCGCCCATTGC
         TGCCCTACTGGCTGCTGGTGTTCCTGGCTGCCCTCAATGCCCTGCTGCAGTGGCTGCTGC
         [G,A]
         GCCACTGGTGCTCTACGCACCCCTGCTGAACCCCTACACGCTGGCCGTGGCCAACACCAC
         CTTCACCGTCAGCACCGACAAGGCTCAGCGCCATTTCGGCTATGAGCCCCTGTTCTCGTG
         GGAGGATAGCCGGACCCGCACCATTCTCTGGGTACAGGCCGCTACGGGTTCAGCCCAGTG
         ACGGTGGGGCTGGGGCCTGGAGGCCCAGATACAGCACATCCACCCAGGTCCCGAGCCCTC
         ACACCCTGGACGGGAAGGGACAGCTGCATTCCAGAGCAGGAGGCAGGGCTTCTGGGGCCA
6293     CACCCCATGTCCGCCTCCCCACGGCGCCCATCCCACGTGGGGACAGAAGGAAGTGAGCAC
         ACGGCACACCCGCTGTTGGATTGGTTGCTATTTCTCCCGTCCCACAGGGCCTGACCTGGC
         CCAGGGTGGGGTGGGGGGCTCTGGGGACAGGACATGCAGGGAGGAAGGGGGGGGCAGGAT
         TTTCCTGTGTTTTATCCATTTGCAAGTTGGTCACCAATAGAAATGGGACTCTGAGGGCTA
         ACAGAAATGGGACTCTGAGGGCTAACAGGAGAGGGCGGCCTGGCTCTGGGCCCCAGCCAG
         [G,A]
         CCCCAGGAGTCCTGTCCCCTCTGAGAAGGGGAGGGAGAGAGCTCTAGAAACCAACGGAGA
         AACAGAGAAGGGGGCAGGGGCTCATGTCAGCAAACACGGCTACATCACGTGACACGCCAG
         TGACACAGAAACACACGCCAACGCACACGGCTGCACAGCGGGCAGGGGCGGTTAGGGGAA
         AGGGAGCCGGGGCCACCCATCTTGTCCTCTGCAGGGCGGGCTGGGGGGCAGGGTGAATGC
         ATAGAACACATCATGTGTACACGCTCAGGGCGTGGCAAGAGCGTGCGTCGACCCACGGGT

Chromosome map:
Chromosome 12
```

FIG.3E

SEQUENCE LISTING

```
<160> NUMBER OF SEQ ID NOS: 4

<210> SEQ ID NO 1
<211> LENGTH: 2071
<212> TYPE: DNA
<213> ORGANISM: Human

<400> SEQUENCE: 1
tggaggagcc agcggaagga cggtgtgcgg gccggccagc cctggacgaa agaagagggc      60
ccctccaggc cagtctgggc accctgggat agcggctgca gccaggcatg gccgactctg     120
cacaggccca gaagctggtg tacctggtca caggggggctg tggcttcctg ggagagcacg    180
tggtgcgaat gctgctgcag cgggagcccc ggctcgggga gctgcgggtc tttgaccaac     240
acctgggtcc ctggctggag gagctgaaga caggtacccg gaacgtgatc gaggcttgtg     300
tgcagaccgg aacacggttc ctggtctaca ccagcagcat ggaagttgtg gggcctaaca     360
ccaaaggtca ccccttctac aggggcaacg aagacacccc atacgaagca gtgcacaggc     420 accctatcc ttgcagcaag gccctggccg agtggctggt cctggaggcc aacgggagga    480
aggtccgtgg ggggctgccc ctggtgacgt gtgcccttcg tcccacgggc atctacggtg     540
aaggccacca gatcatgagg gacttctacc gccagggcct gcgcctggga ggttggctct     600
tccgggccat cccggcctct gtggagcatg gccgggtcta tgtgggcaat gttgcctgga     660
tgcacgtgct ggcagcccgg gagctggagc agcgggcagc cctgatgggc ggccaggtat     720
acttctgcta cgatggatca ccctacagga gctacgagga tttcaacatg gagttcctgg     780
gcccctgcgg actgcggctg gtgggcgccc gcccattgct gccctactgg ctgctggtgt     840
tcctggctgc cctcaatgcc ctgctgcagt ggctgctgcg gccactggtg ctctacgcac     900
ccctgctgaa ccctacacg ctggccgtgg ccaacaccac cttcaccgtc agcaccgaca    960
aggctcagcg ccatttcggc tatgagcccc tgttctcgtg ggaggatagc cggaccccgca    1020 ccattctctg ggtacaggcc gctacgggtt cagcccagtg acgtgggggc tggggcctgg    1080
aggcccagat acagcacatc cacccaggtc ccgagccctc acaccctgga cgggaaggga   1140
cagctgcatt ccagagcagg aggcagggct ctggggccag aatggctgtc cttgtcgtag   1200
agccctccac atttttctttt tcttttttga gacagggtct tgctctgtca cccagactgg   1260
agtgcagtgg tgtgatcata gctcactgca ccctcaacct cctgggttca agcaatcctc   1320
ctgcctcagc ctcctgaaca gctgggacca caggtgcacg ccaccatacc tggcttttt   1380 ttgttgcttt tagagacagg gtctcactat attgctcaag gctggacttg aactcctggg   1440
ctcaagtgat cttcccacgt gggcctccca aaacgctgga actacaagtg tgagccaccg   1500
```

-continued

```
cgcctggccc accgcctctc cacattttca atccaggagc cttgagtctg tggctgtgtc    1560
ctgacacctc cagagttctg agggccgtca ggacacggga gggtttgggg acagagtgtc    1620
cttcctctgt cctatcatca ccagtcctga tggccgcttg gtgagtgtct ggtgccctgg    1680
tggcttgccc cagctctctt gtggctttct gagcaggaag cgagcactag gctccacagg    1740
cttacgctgt gtctcctgcc agccacacag cgacccatcg gtgcagagtg cagacgcggg    1800
tgtggttcct ccagcccacc tcagtccctc tttgggaggt gatgttccca ttgtttttca    1860
aaggcctcac cttcaactgt tctgttttag aattcccctc tggagggcta tggcctccct    1920
atggtttcac ttcccaccta cttctaccta agttccttcc cagcacatcg ccagccctgg    1980
gcctggggat gtccccaatg ctgtacctgg ctgaccccgg attaaaagcc tcatccacga    2040
aaaaaaaaaa aaaaaaaaa aaaaaaaaa a                                     2071
```

<210> SEQ ID NO 2
<211> LENGTH: 317
<212> TYPE: PRT
<213> ORGANISM: Human

<400> SEQUENCE: 2

```
Met Ala Asp Ser Ala Gln Ala Gln Lys Leu Val Tyr Leu Val Thr Gly
  1               5                  10                  15

Gly Cys Gly Phe Leu Gly Glu His Val Val Arg Met Leu Leu Gln Arg
             20                  25                  30

Glu Pro Arg Leu Gly Leu Arg Val Phe Asp Gln His Leu Gly Pro
         35                  40                  45

Trp Leu Glu Glu Leu Lys Thr Gly Thr Arg Asn Val Ile Glu Ala Cys
     50                  55                  60

Val Gln Thr Gly Thr Arg Phe Leu Val Tyr Thr Ser Ser Met Glu Val
 65                  70                  75                  80

Val Gly Pro Asn Thr Lys Gly His Pro Phe Tyr Arg Gly Asn Glu Asp
                 85                  90                  95

Thr Pro Tyr Glu Ala Val His Arg His Pro Tyr Pro Cys Ser Lys Ala
            100                 105                 110

Leu Ala Glu Trp Leu Val Leu Glu Ala Asn Gly Arg Lys Val Arg Gly
        115                 120                 125

Gly Leu Pro Leu Val Thr Cys Ala Leu Arg Pro Thr Gly Ile Tyr Gly
    130                 135                 140

Glu Gly His Gln Ile Met Arg Asp Phe Tyr Arg Gln Gly Leu Arg Leu
145                 150                 155                 160

Gly Gly Trp Leu Phe Arg Ala Ile Pro Ala Ser Val Glu His Gly Arg
                165                 170                 175

Val Tyr Val Gly Asn Val Ala Trp Met His Val Leu Ala Ala Arg Glu
            180                 185                 190

Leu Glu Gln Arg Ala Ala Leu Met Gly Gly Gln Val Tyr Phe Cys Tyr
        195                 200                 205

Asp Gly Ser Pro Tyr Arg Ser Tyr Glu Asp Phe Asn Met Glu Phe Leu
    210                 215                 220

Gly Pro Cys Gly Leu Arg Leu Val Gly Ala Arg Pro Leu Leu Pro Tyr
225                 230                 235                 240

Trp Leu Leu Val Phe Leu Ala Ala Leu Asn Ala Leu Leu Gln Trp Leu
                245                 250                 255

Leu Arg Pro Leu Val Leu Tyr Ala Pro Leu Leu Asn Pro Tyr Thr Leu
            260                 265                 270
```

```
Ala Val Ala Asn Thr Thr Phe Thr Val Ser Thr Asp Lys Ala Gln Arg
        275                 280                 285

His Phe Gly Tyr Glu Pro Leu Phe Ser Trp Glu Asp Ser Arg Thr Arg
        290                 295                 300

Thr Ile Leu Trp Val Gln Ala Ala Thr Gly Ser Ala Gln
305                 310                 315

<210> SEQ ID NO 3
<211> LENGTH: 7301
<212> TYPE: DNA
<213> ORGANISM: Human

<400> SEQUENCE: 3
atttgcatta gccggtggca gccaacaggt gcctgttttg gagagaggtc cagggaggag      60
agatgagcag ggtgccgttg gtgacatggc cagtcatttc aggagctgcc ccaaccccag     120
acttgcccca gcagtccggg accccactgt gaccaggcag atgctcgaag gagtcagtgg     180
ctctcttacc cagtgcagat ttccctggag ttccctgcgg gtgacttaga atggccacca     240
gaggcttagg atgctgcccc aaagaggag ggctcctgga agcagagtcg agagagtcag      300
tgccgggtta gcgggagctg gaggcagagc tgcagctcca ggcctggtgg gcgtggacct     360
ggggtgctgg ctgcaggcg tgctcagggg caggaagtgg gggactcttc cctgaccatc      420
gcatctcacc ctggcagatg gtggccgaca tgcgggagaa gcgctacgtg caggagggca     480
ttggcagcag ctacctgttc cgggtggacc acgacaccat catcgatgcc accaagtgtg     540
gcaacctggc cagattcatc aaccactgct gcacggtgcg ccaggggcca gccggggcag     600
gagttggggg tcggtggggg tggccacggc tcacacgccc ttccatccgc agcctaactg     660
ctacgccaag gtcatcacca tcgagtccca aagaagatc gtgatctact ccaagcagcc      720
cattggcgtg gacgaggaga tcacctacga ctacaagttc ccactggaag acaacaagat     780
cccgtgtctg tgtggcacag agagctgccg gggctcccta aactgaggtg gggcaggatg     840
ggtgcccaca cccctattta ttcccctgg tgccctgagc tcccagcacc ccccagcct      900 tagtgggctc agcagggccc acatgccccc atctccaagc gtgggtgtgg gggccccaag     960
cccagcgagg gagcctcagt ccctggaggc agcttctgcc tctcctgtcg ccctgccca     1020 ccaccccctg attgttttc tttgcggaga agaagctgta aatgttttgt agcagccagc     1080
agctgtttcc tgtggaaacc tggggtgccg gcctgtacag attctgtcct ggggggctac     1140
acagtcctct cgctttgtgt taatgggac ttcccttac gccctgcgtg taccctccc       1200 cagtttaggg gtctctgggg cagtggccat gttctccccc tgggggggct ctgcaccccc     1260
agtcctgggg actccgtgcc tggaaccctg cctcatctgt tcctgccaga ccctgagggt     1320
cacccttcca ccctggtgtc actccccggc tcagccaggc caggatggcg gggtgggtcc     1380
cttttgctgg gctggactgt acatatgtta atagcgcaaa cccgacgcca cattttata     1440 attgtgatta aactttattg tacaaaagtg tttggtcggt gtatttgggc aggagcgagg     1500
ggttgggggt agagggcacg gagggttgtg caagttgaag agaggaaaa gtgggtacct     1560 gaagtgtggg gcaggtaaag gggccttcag gcaagagccc agacctgcag agacagtccg     1620
agactgtctc ggaccccctg acaggctgca gcagccgcac ccgcaccagg aatacccac      1680 cagtgcccgc cagggtggtg ccaaggtcag gcctccccctt cctacaatca cagctgcagc    1740
tggacctccg gcctcctggg aagcccagca ggagggaagg cctgaggtca cactgtggga    1800
tgaggtcacc gctggctcca cccacagccc cagacccctt cagcccactc tgcaagttcg     1860
```

```
agcttcatcc ccaccaagtt ctccgctgga cccagatgcc agtggagcac agagcggccg    1920 ccaggggggcg ccttggggca agagtggtgg gggttgtggc tgggcgggtc tctgttcctg   1980
gaatggggca ggagggagaa ggaggagcca gcggaaggac ggtgtgcggg ccggccagcc    2040
ctggacgaaa gaagagggcc cctccaggcc agtctgggca ccctgggata gcggctgcag    2100
gtaggcagag gcgctgccag tgcccaggtg gcctttccct ccatccggcc cttcccacct    2160
tcctataacc ttccctccac ctccctcaac tcctggcctc ccacccttt tactgccttc     2220 aaatctctct ccctaaaccc tgaccccttc ctgcaccca agcccgcccc tctctccgta    2280
actcagccat cagcaggggc agacggcagg tggcctggtt gctgcagctc ccaggatcag    2340
ctctgccctc ccgccaaacg ccagcctcgt caccgctcca gggcacctcc agcagtaaca    2400
ggtggttgca gcaggtggca gccagcccct ggatgagcca aggtctcttc cccagccagg    2460
catggccgac tctgcacagg cccagaagct ggtgtacctg gtcacagggg gctgtggctt    2520
cctgggagag cacgtggtgc gaatgctgct gcagcgggag ccccggctcg gggagctgcg    2580 ggtcttttgac caacacctgg gtccctggct ggaggagctg aagacaggtt cttgttgggg    2640
gagcttgtgg tggagagggt gtggacgctt ccccaaccct tcccaagctg ggatccccac    2700
ccctgcagtg gaacagatga tgctggtttc tgtccacatg gatgggtcga gtgagtcaca    2760
ttgggaacgt gactccaggg tggaagatga acccagcctc tggcctctgg ccccagctct    2820
gacatggcct gtgtcctcca accccggcca gggcctgtga gggtgactgc catccagggg    2880
gacgtgaccc aggcccatga ggtggcagca gctgtggccg gagcccatgt ggtcatccac    2940
acggctgggc tggtagacgt gtttggcagg ccagtcccca agaccatcca tgaggtcaac    3000
gtgcagggtg aggagctctg gacactcctg gccatcttgc ctgtttgttc cccactctgt    3060
ctttggcctt gacctccggt gactcccctg ggacaagttg tcctattgac agccctgccc    3120
ccgcctcccc tgacctgtca tggttttccc tggacctggg atggggagga ggaagatgca    3180
gagagggaag aagctgcagc ttggatacgc ctcctcctct gccaggtacc cggaacgtga    3240
tcgaggcttg tgtgcagacc ggaacacggt tcctggtcta caccagcagc atggaagttg    3300
tggggcctaa caccaaaggt caccccttct acaggtgagt ggcaggccct cttgtcctct    3360
aagagcccat ttccctcagc attgagtctt ccttctcctc ccaccagggg caacgaagac    3420
accccatacg aagcagtgca caggcacccc tatccttgca gcaaggccct ggccgagtgg    3480
ctggtcctgg aggccaacgg gaggaaggtg agcccagaaa aaggaggcgc agagatgggg    3540
ctcctgccct gcacaccccc ttaccctgcc agcccaagga ggccggggcc gagagcaagc    3600
tgtcgggtcc caggtctcag cagtacctgc ctttgccacc aggtccgtgg ggggctgccc    3660
ctggtgacgt gtgcccttcg tcccacgggc atctacggtg aaggccacca gatcatgagg    3720
gacttctacc gccagggcct cgcctggga ggttggctct ccgggccat cccggcctct     3780 gtggagcatg gccgggtcta tgtgggtgag gactgggcta ggcaggggga ggctgagaat    3840
atggcaggag gacttgctct agaagggggc aggacccaca tggccctggg agagaagtgt    3900
ggactctggc tagaaaaata tggtctatac atgggccaag gtagactgtg attatgtctc    3960
cacagcctgc agagaataca ggatccatgc aagttgggac attaaaaagt gtatcatagg    4020
ctacagagaa gattgcagct atgggagcag ccattcccca ggagaggaga ggagagggac    4080
agtgtgtaca cagcactaaa agggctgggt tcagtggctc gcatctataa tcccagcact    4140
ttaggaggct gaggcgggag gatggcctga gcccaggagt tggaggctgc agtgagctat    4200
gaccgcacca ctgcactcca gcctggatga cagagacaga ccctgtctct aaaactttt    4260
```

-continued

| | |
|---|---|
| ttaaaggaag tagcatctac acagggaata aggtcacctg ccactccatc ctgcagtccc | 4320 |
| caagcctctc agggcccacc acgcaggtcc tggtttctct atcctctccc caggttcttt | 4380 |
| gcagatgcag gctggcccag gagagcaagt gactaccagg gcgagggaga aggcagcctt | 4440 |
| tcccaggctg ctgtggggat gtgggcggca actacctggg cccaaagagg gggtggccca | 4500 |
| ggagagcagc ctcgatgtgg tgttgcaagg gcactcaggt gtgtccgc ctctcttccg | 4560 |
| ccaccggcag gcaatgttgc ctggatgcac gtgctggcag cccgggagct ggagcagcgg | 4620 |
| gcagccctga tgggcggcca ggtatacttc tgctacgatg gatcaccta caggagctac | 4680 |
| gaggatttca acatggagtt cctgggcccc tgcggactgc ggctggtggg cgcccgccca | 4740 |
| ttgctgccct actggctgct ggtgttcctg gctgccctca tgccctgct gcagtggctg | 4800 |
| ctgcggccac tggtgctcta cgcacccctg ctgaaccct acacgctggc cgtggccaac | 4860 |
| accaccttca ccgtcagcac cgacaaggct cagcgccatt tcggctatga gcccctgttc | 4920 |
| tcgtgggagg atagccggac ccgcaccatt ctctgggtac aggccgctac gggttcagcc | 4980 |
| cagtgacggt ggggctgggg cctggaggcc cagatacagc acatccaccc aggtcccgag | 5040 |
| ccctcacacc ctggacggga aggacagct gcattccaga gcaggaggca gggcttctgg | 5100 |
| ggccagaatg gctgtccttg tcgtagagcc ctccacattt tctttttctt ttttgagaca | 5160 |
| gggtcttgct ctgtcaccca gactggagtg cagtggtgtg atcatagctc actgcaccct | 5220 |
| caacctcctg ggttcaagca atcctcctgc ctcagcctcc ttgaacagct gggaccacag | 5280 |
| gtgcacgcca ccacacctgg ctttttttg ttgttttag agacagggtc tcactatatt | 5340 |
| gctcaggctg gtcttgaact cctgggctca agtgatcttc ccacgtgggc ctcccaaaac | 5400 |
| gctggaacta caagtgtgag ccaccgcgcc tggcccaagc cctccacatt ttcaatccag | 5460 |
| gagccttgag tctgtgttgt gtcctgacac ctccaagttc tagggccgtc aggacacggg | 5520 |
| agggtttggg gacagagtgt ccttcctctg tcctctcatc ccagtcctga tggccgcttg | 5580 |
| gtgagtgtct ggtgccctgg tggcctgccc cagctctctt ctggctttct gagcaggaag | 5640 |
| cgagcagagg ctccacaggc ttacgctgct ccctgacag ccacgcgca ccctcggtgc | 5700 |
| agagtgcaga ggcggctctg gttcctccag ccacctcagt ccctctttgg gaggtgatgt | 5760 |
| tcccattgtt tttcaaaggc ctcaccttca actgtctgtc ttagaattcc cctctggagg | 5820 |
| gctatggcct ccctatgctt tcacttccca cctctctacc taagttcctt cccagcacat | 5880 |
| cgccagccct gggcctgggg atgtcccaa tgctgtacct ggctgacccc ggattaaaag | 5940 |
| cctcatccac gaccgtgtcc atctgtctgt ccagctctcc ctcccatccc cccaccccat | 6000 |
| gtccgcctcc ccacgcgcc catcccacgt ggggacagaa ggaagtgagc acacggcaca | 6060 |
| cccgctgttg gattggttgc tatttctccc gtcccacagg gcctgacctg gcccagggtg | 6120 |
| gggtgggggg ctctggggac aggacatgca gggaggaagg gggggcagg attttcctgt | 6180 |
| gttttatcca tttgcaagtt ggtcaccaat agaaatggga ctctgagggc taacagaaat | 6240 |
| gggactctga gggctaacag gagagggcgg cctggctctg ggcccagcc aggcccagg | 6300 |
| agtcctgtcc cctctgagaa gggagggag agagctctag aaaccaacgg agaaacagag | 6360 |
| aaggggcag gggctcatgt cagcaaacac ggctacatca cgtgacacgc cagtgacaca | 6420 |
| gaaacacacg ccaacgcaca cggctgcaca gcgggcaggg gcggttaggg gaaagggagc | 6480 |
| cggggccacc catcttgtcc tctgcagggc gggctgggg gcaggtgaa tgcatagaac | 6540 |
| acatcatgtg tacacgctca gggcgtggca agagcgtgcg tcgacccacg ggtacatggg | 6600 |
| atggacacgc agtgtgcttc atgagggggtg ggaacaggga ggagggggaa gaggaagcac | 6660 |

-continued

```
tgagccctgg ccaggcccgg gaccacccgc agggcacacg tggggcacat gtgggctcaa    6720
tggttgcagg cgcctgggca ggtagcacac atttgtccaa gaacatgcaa aagacaccag    6780
cctccagaca acatgccagg acgcacacag acagcagcca acaagcaggc acatcatagg    6840
atgtggagga cgcatagaaa gggcacagca gaccttagag gatcccctgg tccacctgag    6900
gcccagagat gggcagctgt gggcccaatg ccactccagg tgggggagt ggtgccccag    6960 ccacgcttca acccttctcc tgtggcccca aggccgtggg acttccggaa acacctgggc    7020
tgaatggggg tcctgtccag gcggccggaa gaggggactg ggggctgggg cctgctctga    7080
tgtctcccaa gcagcccgag atgggagcag gagggccgtg gccagacttg ggcagactt    7140 cctgtcctgc agagggcgt tctgggaagg acaggcagg cccccagctc aggacagccc    7200 acctgggtt acgcacgtgg ccacactgac acacacacag gacaagggag agctcggctg    7260
tctgagctcg ggtagaggtg gagggtact gtgttctggg a                        7301
```

<210> SEQ ID NO 4
<211> LENGTH: 369
<212> TYPE: PRT
<213> ORGANISM: Human

<400> SEQUENCE: 4

```
Met Ala Asp Ser Ala Gln Ala Gln Lys Leu Val Tyr Leu Val Thr Gly
  1               5                  10                  15

Gly Cys Gly Phe Leu Gly Glu His Val Val Arg Met Leu Leu Gln Arg
                 20                  25                  30

Glu Pro Arg Leu Gly Glu Leu Arg Val Phe Asp Gln His Leu Gly Pro
             35                  40                  45

Trp Leu Glu Glu Leu Lys Thr Gly Pro Val Arg Val Thr Ala Ile Gln
         50                  55                  60

Gly Asp Val Thr Gln Ala His Glu Val Ala Ala Val Ala Gly Ala
 65                  70                  75                  80

His Val Val Ile His Thr Ala Gly Leu Val Asp Val Phe Gly Arg Ala
                 85                  90                  95

Ser Pro Lys Thr Ile His Glu Val Asn Val Gln Gly Thr Arg Asn Val
                100                 105                 110

Ile Glu Ala Cys Val Gln Thr Gly Thr Arg Phe Leu Val Tyr Thr Ser
            115                 120                 125

Ser Met Glu Val Val Gly Pro Asn Thr Lys Gly His Pro Phe Tyr Arg
        130                 135                 140

Gly Asn Glu Asp Thr Pro Tyr Glu Ala Val His Arg His Pro Tyr Pro
145                 150                 155                 160

Cys Ser Lys Ala Leu Ala Glu Trp Leu Val Leu Glu Ala Asn Gly Arg
                165                 170                 175

Lys Val Arg Gly Gly Leu Pro Leu Val Thr Cys Ala Leu Arg Pro Thr
            180                 185                 190

Gly Ile Tyr Gly Glu Gly His Gln Ile Met Arg Asp Phe Tyr Arg Gln
        195                 200                 205

Gly Leu Arg Leu Gly Gly Trp Leu Phe Arg Ala Ile Pro Ala Ser Val
    210                 215                 220

Glu His Gly Arg Val Tyr Val Gly Asn Val Ala Trp Met His Val Leu
225                 230                 235                 240

Ala Ala Arg Glu Leu Glu Gln Arg Ala Ala Leu Met Gly Gly Gln Val
                245                 250                 255
```

-continued

```
Tyr Phe Cys Tyr Asp Gly Ser Pro His Arg Ser Tyr Glu Asp Phe Asn
            260                 265                 270

Met Glu Phe Leu Gly Pro Cys Gly Leu Arg Leu Val Gly Ala Arg Pro
            275                 280                 285

Leu Leu Pro Tyr Trp Leu Leu Val Phe Leu Ala Ala Leu Asn Ala Leu
            290                 295                 300

Leu Gln Trp Leu Leu Arg Pro Leu Val Leu Tyr Ala Pro Leu Leu Asn
305                 310                 315                 320

Pro Tyr Thr Leu Ala Val Ala Asn Ala Thr Phe Thr Val Ser Thr Asp
                325                 330                 335

Lys Ala Gln Arg His Phe Gly Tyr Glu Pro Leu Phe Ser Trp Glu Asp
            340                 345                 350

Ser Arg Thr Arg Thr Ile Leu Trp Val Gln Ala Ala Thr Gly Ser Ala
            355                 360                 365

Gln
```

US 6,326,180 B1

ISOLATED HUMAN ENZYME, NUCLEIC ACID MOLECULES ENCODING HUMAN ENZYME, AND USES THEREOF

FIELD OF THE INVENTION

The present invention is in the field of enzyme proteins that are related to the steroid oxidoreductase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Many human enzymes serve as targets for the action of pharmaceutically active compounds. Several classes of human enzymes that serve as such targets include helicase, steroid esterase and sulfatase, convertase, synthase, dehydrogenase, monoxygenase, transferase, kinase, glutanase, decarboxylase, isomerase and reductase. It is therefore important in developing new pharmaceutical compounds to identify target enzyme proteins that can be put into high-throughput screening formats. The present invention advances the state of the art by providing novel human drug target enzymes related to the steroid oxidoreductase subfamily.

The present invention has substantial similarity to 3β-hydroxy-5-C27-steroid oxidoreductase ($C_{27}$ 3β-HSD). 3β-hydroxy-5-C27-steroid oxidoreductase involves in the synthesis of bile acids.

Bile acids are important components of normal physiology with essential functions in the liver and small intestine. Their synthesis in the liver provides a metabolic pathway for the catabolism of cholesterol and their detergent properties promote the solubilization of essential nutrients and vitamins in the small intestine. The synthesis of bile acids was thought to involve as many as three separate pathways. Each pathway differs in the initial steps and in the involvement of distinct sterol 7-hydroxylase enzymes that add an essential hydroxyl group to carbon seven of the sterol ring. After the addition of this group, the next step in each pathway is catalyzed by a 3β-hydroxy-5-C27-steroid oxidoreductase, which isomerizes the 5 bond to the 4 position and oxidizes the 3β-hydroxyl group to a 3-oxo moiety on intermediates with 27 carbon atoms.

The 3β-HSD enzyme family consists of a large number of proteins that are present in both prokaryotes and eukaryotes. They are proposed to play a wide variety of anabolic and catabolic roles in intermediary metabolism, and, consistent with this broad function, they are expressed in abundance in organisms ranging from viruses to humans.

$C_{27}$ 3β-HSD enzyme deficiency is marked by accumulation of $C_{27}$ sterol intermediates of bile acid synthesis, progressive intrahepatic cholestasis, and no endocrine abnormalities. Inherited conditions that prevent the synthesis of bile acids can cause the accumulation of cholesterol and liver dysfunction (cholestasis), underscoring the essential role of bile acids in metabolism. Progressive neonatal intrahepatic cholestasis is marked by jaundice, fat-soluble vitamin deficiency, and lipid malabsorption and is a rare condition of diverse etiologies. Among the causes of this disorder are inborn errors of metabolism that affect the production and secretion of bile. In the absence of a normal bile flow and bile acid pool size, the end products of heme metabolism are not secreted, and their accumulation causes the characteristic jaundice. Dietary fat-soluble vitamins are not effectively taken up in the intestine, leading to deficiencies in hemostasis, and hydrophobic lipids such as long-chain fatty acids and cholesterol are poorly absorbed causing fatty stools. It has been reported that a deficiency of this enzyme can be treated by oral administration of bile acids. For a review relate to the oxidoreductase, see Schwarz et al., J Clin Invest 2000 Nov; 106(9):1175–84.

Enzyme proteins, particularly members of the steroid oxidoreductase subfamily, are a major target for drug action and development. Accordingly, it is valuable to the field of pharmaceutical development to identify and characterize previously unknown members of this subfamily of enzyme proteins. The present invention advances the state of the art by providing previously unidentified human enzyme proteins, and the polynucleotides encoding them, that have homology to members of the steroid oxidoreductase subfamily. These novel compositions are useful in the diagnosis, prevention and treatment of biological processes associated with human diseases.

SUMMARY OF THE INVENTION

The present invention is based in part on the identification of amino acid sequences of human enzyme peptides and proteins that are related to the steroid oxidoreductase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate enzyme activity in cells and tissues that express the enzyme. Experimental data as provided in FIG. 1 indicates expression in humans in the brain, kidney, colon and uterus.

DESCRIPTION OF THE FIGURE SHEETS

FIG. 1 provides the nucleotide sequence of a cDNA molecule sequence that encodes the enzyme protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in the brain, kidney, colon and uterus.

FIG. 2 provides the predicted amino acid sequence of the enzyme of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the enzyme protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs, were identified at 4 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a enzyme protein or part of a enzyme protein and are related to the steroid oxidoreductase subfamily. Utilizing these sequences, additional genomic sequences were assembled and transcript and/or cDNA sequences were isolated and characterized. Based on this analysis, the present invention provides amino acid sequences of human enzyme peptides and proteins that are related to the steroid oxidoreductase subfamily, nucleic acid sequences in the form of transcript sequences, cDNA sequences and/or genomic sequences that encode these enzyme peptides and proteins, nucleic acid variation (allelic information), tissue distribution of expression, and information about the closest art known protein/peptide/domain that has structural or sequence homology to the enzyme of the present invention.

In addition to being previously unknown, the peptides that are provided in the present invention are selected based on their ability to be used for the development of commercially important products and services. Specifically, the present peptides are selected based on homology and/or structural relatedness to known enzyme proteins of the steroid oxidoreductase subfamily and the expression pattern observed. Experimental data as provided in FIG. 1 indicates expression in humans in the brain, kidney, colon and uterus. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known steroid oxidoreductase family or subfamily of enzyme proteins.

Specific Embodiments

Peptide Molecules

The present invention provides nucleic acid sequences that encode protein molecules that have been identified as being members of the enzyme family of proteins and are related to the steroid oxidoreductase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the enzyme peptides of the present invention, enzyme peptides, or peptides/proteins of the present invention.

The present invention provides isolated peptide and protein molecules that consist of, consist essentially of, or comprise the amino acid sequences of the enzyme peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the enzyme peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated enzyme peptide can be purified from cells that naturally express it, purified from cells that have been altered to express it (recombinant), or synthesized using known protein synthesis methods. Experimental data as provided in FIG. 1 indicates expression in humans in the brain, kidney, colon and uterus. For example, a nucleic acid molecule encoding the enzyme peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the enzyme peptides of the present invention are the naturally occurring mature proteins. A brief description of how various types of these proteins can be made/isolated is provided below.

The enzyme peptides of the present invention can be attached to heterologous sequences to form chimeric or fusion proteins. Such chimeric and fusion proteins comprise a enzyme peptide operatively linked to a heterologous protein having an amino acid sequence not substantially homologous to the enzyme peptide. "Operatively linked" indicates that the enzyme peptide and the heterologous protein are fused in-frame. The heterologous protein can be fused to the N-terminus or C-terminus of the enzyme peptide.

In some uses, the fusion protein does not affect the activity of the enzyme peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant enzyme peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A enzyme peptide-encoding nucleic acid can be cloned into such an expression vector such that the fusion moiety is linked in-frame to the enzyme peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the enzyme peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the enzyme peptides of the present invention as well as being encoded by the same genetic locus as the enzyme peptide provided herein. As indicated by the data presented in FIG. 3, the map position was determined to be on chromosome 12 by ePCR.

Allelic variants of a enzyme peptide can readily be identified as being a human protein having a high degree (significant) of sequence homology/identity to at least a portion of the enzyme peptide as well as being encoded by the same genetic locus as the enzyme peptide provided herein. Genetic locus can readily be determined based on the genomic information provided in FIG. 3, such as the genomic sequence mapped to the reference human. As indicated by the data presented in FIG. 3, the map position was determined to be on chromosome 12 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a enzyme peptide encoding nucleic acid molecule under stringent conditions as more fully described below.

FIG. 3 provides information on SNPs that have been found in the gene encoding the enzyme of the present invention. SNPs were identified at 4 different nucleotide positions in exon, introns and regions 5' and 3' of the ORF. Such SNPs in introns and outside the ORF may affect control/regulatory elements. Changes in the amino acid sequence caused by these SNPs is indicated in FIG. 3 and can readily be determined using the universal genetic code and the protein sequence provided in FIG. 2 as a reference.

Paralogs of a enzyme peptide can readily be identified as having some degree of significant sequence homology/identity to at least a portion of the enzyme peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a enzyme peptide encoding nucleic acid molecule under moderate to stringent conditions as more fully described below.

Orthologs of a enzyme peptide can readily be identified as having some degree of significant sequence homology/identity to at least a portion of the enzyme peptide as well as being encoded by a gene from another organism. Preferred orthologs will be isolated from mammals, preferably primates, for the development of human therapeutic targets and agents. Such orthologs will be encoded by a nucleic acid sequence that will hybridize to a enzyme peptide encoding nucleic acid molecule under moderate to stringent conditions, as more fully described below, depending on the degree of relatedness of the two organisms yielding the proteins.

Non-naturally occurring variants of the enzyme peptides of the present invention can readily be generated using recombinant techniques. Such variants include, but are not limited to deletions, additions and substitutions in the amino acid sequence of the enzyme peptide. For example, one class of substitutions are conserved amino acid substitution. Such substitutions are those that substitute a given amino acid in a enzyme peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie etal., *Science* 247:1306–1310 (1990).

Variant enzyme peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as enzyme activity or in assays such as an in vitro proliferative activity. Sites that are critical for binding partner/substrate binding can also be determined by structural analysis such as crystallization, nuclear magnetic resonance or photoaffinity labeling (Smith et al, *J. Mol. Biol.* 224:899–904 (1992); de Vos et al. *Science* 255:306–312 (1992)).

The present invention further provides fragments of the enzyme peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a enzyme peptide. Such fragments can be chosen based on the ability to retain one or more of the biological activities of the enzyme peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the enzyme peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in enzyme peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al (*Ann. N.Y. Acad. Sci.* 663:48–62 (1992)).

Accordingly, the enzyme peptides of the present invention also encompass derivatives or analogs in which a substituted amino acid residue is not one encoded by the genetic code, in which a substituent group is included, in which the mature enzyme peptide is fused with another compound, such as a compound to increase the half-life of the enzyme peptide (for example, polyethylene glycol), or in which the additional amino acids are fused to the mature enzyme peptide, such as a leader or secretory sequence or a sequence for purification of the mature enzyme peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a enzyme-effector protein interaction or enzyme-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, enzymes isolated from humans and their human/mammalian orthologs serve as targets for identifying agents for use in mammalian therapeutic applications, e.g. a human drug, particularly in modulating a biological or pathological response in a cell or tissue that expresses the enzyme. Experimental data as provided in FIG. 1 indicates that the enzymes of the present invention are expressed in humans in the brain, kidney, colon, uterus detected by a virtual northern blot. A large percentage of pharmaceutical agents are being developed that modulate the activity of enzyme proteins, particularly members of the steroid oxidoreductase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the brain, kidney, colon and uterus. Such uses can readily be determined using the information provided herein, that which is known in the art, and routine experimentation.

The proteins of the present invention (including variants and fragments that may have been disclosed prior to the present invention) are useful for biological assays related to enzymes that are related to members of the steroid oxidoreductase subfamily. Such assays involve any of the known enzyme functions or activities or properties useful for diagnosis and treatment of enzyme-related conditions that are specific for the subfamily of enzymes that the one of the present invention belongs to, particularly in cells and tissues that express the enzyme. Experimental data as provided in FIG. 1 indicates that the enzymes of the present invention are expressed in humans in the brain, kidney, colon, uterus detected by a virtual northern blot.

The proteins of the present invention are also useful in drug screening assays, in cell-based or cell-free systems. Cell-based systems can be native, i.e., cells that normally express the enzyme, as a biopsy or expanded in cell culture. Experimental data as provided in FIG. 1 indicates expression in humans in the brain, kidney, colon and uterus. In an alternate embodiment, cell-based assays involve recombinant host cells expressing the enzyme protein.

The polypeptides can be used to identify compounds that modulate enzyme activity of the protein in its natural state or an altered form that causes a specific disease or pathology associated with the enzyme. Both the enzymes of the present invention and appropriate variants and fragments can be used in high-throughput screens to assay candidate compounds for the ability to bind to the enzyme. These compounds can be further screened against a functional enzyme to determine the effect of the compound on the enzyme activity. Further, these compounds can be tested in animal or invertebrate systems to determine activity/effectiveness.

Compounds can be identified that activate (agonist) or inactivate (antagonist) the enzyme to a desired degree.

Further, the proteins of the present invention can be used to screen a compound for the ability to stimulate or inhibit interaction between the enzyme protein and a molecule that normally interacts with the enzyme protein, e.g. a substrate or a component of the signal pathway that the enzyme protein normally interacts (for example, another enzyme). Such assays typically include the steps of combining the enzyme protein with a candidate compound under conditions that allow the enzyme protein, or fragment, to interact with the target molecule, and to detect the formation of a complex between the protein and the target or to detect the biochemical consequence of the interaction with the enzyme protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant enzymes or appropriate fragments containing mutations that affect enzyme function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) enzyme activity. The assays typically involve an assay of events in the signal transduction pathway that indicate enzyme activity. Thus, the phosphorylation of a substrate, activation of a protein, a change in the expression of genes that are up- or down-regulated in response to the enzyme protein dependent signal cascade can be assayed.

Any of the biological or biochemical functions mediated by the enzyme can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the enzyme can be assayed. Experimental data as provided in FIG. 1 indicates that the enzymes of the present invention are expressed in humans in the brain, kidney, colon, uterus detected by a virtual northern blot.

Binding and/or activating compounds can also be screened by using chimeric enzyme proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native enzyme. Accordingly, a different set of signal transduction components is available as an end-point assay for activation. This allows for assays to be performed in other than the specific host cell from which the enzyme is derived.

The proteins of the present invention are also useful in competition binding assays in methods designed to discover compounds that interact with the enzyme (e.g. binding partners and/or ligands). Thus, a compound is exposed to a enzyme polypeptide under conditions that allow the compound to bind or to otherwise interact with the polypeptide. Soluble enzyme polypeptide is also added to the mixture. If the test compound interacts with the soluble enzyme polypeptide, it decreases the amount of complex formed or activity from the enzyme target. This type of assay is particularly useful in cases in which compounds are sought that interact with specific regions of the enzyme. Thus, the soluble polypeptide that competes with the target enzyme region is designed to contain peptide sequences corresponding to the region of interest.

To perform cell free drug screening assays, it is sometimes desirable to immobilize either the enzyme protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of enzyme-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a enzyme-binding protein and a candidate compound are incubated in the enzyme protein-presenting wells and the amount of complex trapped in the well can be quantitated. Methods for detecting such complexes, in addition to those described above for the GST-immobilized complexes, include immunodetection of complexes using antibodies reactive with the enzyme protein target molecule, or which are reactive with enzyme protein and compete with the target molecule, as well as enzyme-linked assays which rely on detecting an enzymatic activity associated with the target molecule.

Agents that modulate one of the enzymes of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of enzyme protein activity identified according to these drug screening assays can be used to treat a subject with a disorder mediated by the enzyme pathway, by treating cells or tissues that express the enzyme. Experimental data as provided in FIG. 1 indicates expression in humans in the brain, kidney, colon and uterus. These methods of treatment include the steps of administering a modulator of enzyme activity in a pharmaceutical composition to a subject in need of such treatment, the modulator being identified as described herein.

In yet another aspect of the invention, the enzyme proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the enzyme and are involved in enzyme activity. Such enzyme-binding proteins are also likely to be involved in the propagation of signals by the enzyme proteins or enzyme targets as, for example, downstream elements of a enzyme-mediated signaling pathway. Alternatively, such enzyme-binding proteins are likely to be enzyme inhibitors.

The two-hybrid system is based on the modular nature of most transcription factors, which consist of separable DNA-binding and activation domains. Briefly, the assay utilizes two different DNA constructs. In one construct, the gene that codes for a enzyme protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a enzyme-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the enzyme protein.

This invention further pertains to novel agents identified by the above-described screening assays. Accordingly, it is within the scope of this invention to further use an agent identified as described herein in an appropriate animal model. For example, an agent identified as described herein (e.g., a enzyme-modulating agent, an antisense enzyme nucleic acid molecule, a enzyme-specific antibody, or a enzyme-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The enzyme proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the brain, kidney, colon and uterus. The method involves contacting a biological sample with a compound capable of interacting with the enzyme protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered enzyme activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the enzyme protein in which one or more of the enzyme functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and enzyme activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the brain, kidney, colon and uterus. Accordingly, methods for treatment include the use of the enzyme protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the enzyme proteins. Antibodies can be prepared from any region of the peptide as described herein. However, preferred regions will include those involved in function/activity and/or enzyme/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the enzymes of the present invention are expressed in humans in the brain, kidney, colon, uterus detected by a virtual northern blot. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the brain, kidney, colon and uterus. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the brain, kidney, colon and uterus. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the brain, kidney, colon and uterus. Thus, where a specific protein has been correlated with expression in a specific tissue, antibodies that are specific for this protein can be used to identify a tissue type.

The antibodies are also useful for inhibiting protein function, for example, blocking the binding of the enzyme peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a enzyme peptide or protein of the present invention (cDNA, transcript and genomic sequence). Such nucleic acid molecules will consist of, consist essentially of, or comprise a nucleotide sequence that encodes one of the enzyme peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the enzyme peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the enzyme proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 12 by ePCR.

FIG. 3 provides information on SNPs that have been found in the gene encoding the enzyme of the present invention. SNPs were identified at 4 different nucleotide positions in exon, introns and regions 5' and 3' of the ORF. Such SNPs in introns and outside the ORF may affect control/regulatory elements. Changes in the amino acid sequence caused by these SNPs is indicated in FIG. 3 and can readily be determined using the universal genetic code and the protein sequence provided in FIG. 2 as a reference.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45C, followed by one or more washes in 0.2× SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs, were identified at 4 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 12 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the enzymes of the present invention are expressed in humans in the brain, kidney, colon, uterus detected by a virtual northern blot. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in enzyme protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a enzyme protein, such as by measuring a level of a enzyme-encoding nucleic acid in a sample of cells from a subject e.g., mRNA or genomic DNA, or determining if a enzyme gene has been mutated. Experimental data as provided in FIG. 1 indicates that the enzymes of the present invention are expressed in humans in the brain, kidney, colon, uterus detected by a virtual northern blot.

Nucleic acid expression assays are useful for drug screening to identify compounds that modulate enzyme nucleic acid expression.

The invention thus provides a method for identifying a compound that can be used to treat a disorder associated with nucleic acid expression of the enzyme gene, particularly biological and pathological processes that are mediated by the enzyme in cells and tissues that express it. Experimental data as provided in FIG. 1 indicates expression in humans in the brain, kidney, colon and uterus. The method typically includes assaying the ability of the compound to modulate the expression of the enzyme nucleic acid and thus identifying a compound that can be used to treat a disorder characterized by undesired enzyme nucleic acid expression. The assays can be performed in cell-based and cell-free systems. Cell-based assays include cells naturally expressing the enzyme nucleic acid or recombinant cells genetically engineered to express specific nucleic acid sequences.

The assay for enzyme nucleic acid expression can involve direct assay of nucleic acid levels, such as mRNA levels, or on collateral compounds involved in the signal pathway. Further, the expression of genes that are up- or down-regulated in response to the enzyme protein signal pathway can also be assayed. In this embodiment the regulatory regions of these genes can be operably linked to a reporter gene such as luciferase.

Thus, modulators of enzyme gene expression can be identified in a method wherein a cell is contacted with a candidate compound and the expression of mRNA determined. The level of expression of enzyme mRNA in the presence of the candidate compound is compared to the level of expression of enzyme mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate enzyme nucleic acid expression in cells and tissues that express the enzyme. Experimental data as provided in FIG. 1 indicates that the enzymes of the present invention are expressed in humans in the brain, kidney, colon, uterus detected by a virtual northern blot. Modulation includes both up-regulation (i.e. activation or agonization) or down-regulation (suppression or antagonization) or nucleic acid expression.

Alternatively, a modulator for enzyme nucleic acid expression can be a small molecule or drug identified using the screening assays described herein as long as the drug or small molecule inhibits the enzyme nucleic acid expression in the cells and tissues that express the protein. Experimental data as provided in FIG. 1 indicates expression in humans in the brain, kidney, colon and uterus.

The nucleic acid molecules are also useful for monitoring the effectiveness of modulating compounds on the expression or activity of the enzyme gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in enzyme nucleic acid expression, and particularly in qualitative changes that lead to pathology. The nucleic acid molecules can be used to detect mutations in enzyme genes and gene expression products such as mRNA. The nucleic acid molecules can be used as hybridization probes to detect naturally occurring genetic mutations in the enzyme gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the enzyme gene associated with a dysfunction provides a diagnostic tool for an active disease or susceptibility to disease when the disease results from overexpression, underexpression, or altered expression of a enzyme protein.

Individuals carrying mutations in the enzyme gene can be detected at the nucleic acid level by a variety of techniques. FIG. 3 provides information on SNPs that have been found in the gene encoding the enzyme of the present invention. SNPs were identified at 4 different nucleotide positions in exon, introns and regions 5' and 3' of the ORF. Such SNPs in introns and outside the ORF may affect control/regulatory elements. Changes in the amino acid sequence caused by these SNPs is indicated in FIG. 3 and can readily be determined using the universal genetic code and the protein sequence provided in FIG. 2 as a reference. As indicated by the data presented in FIG. 3, the map position was determined to be on chromosome 12 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al, *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a enzyme gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant enzyme gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al, *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the enzyme gene in an individual in order to select an appropriate compound or dosage regimen for treatment. FIG. 3 provides information on SNPs that have been found in the gene encoding the enzyme of the present invention. SNPs were identified at 4 different nucleotide positions in exon, introns and regions 5' and 3' of the ORF. Such SNPs in introns and outside the ORF may affect control/regulatory elements. Changes in the amino acid sequence caused by these SNPs is indicated in FIG. 3 and can readily be determined using the universal genetic code and the protein sequence provided in FIG. 2 as a reference.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control enzyme gene expression in cells, tissues, and organisms. A DNA antisense nucleic acid molecule is designed to be complementary to a region of the gene involved in transcription, preventing transcription and hence production of enzyme protein. An antisense RNA or DNA nucleic acid molecule would hybridize to the mRNA and thus block translation of mRNA into enzyme protein.

Alternatively, a class of antisense molecules can be used to inactivate mRNA in order to decrease expression of enzyme nucleic acid. Accordingly, these molecules can treat a disorder characterized by abnormal or undesired enzyme nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the enzyme protein, such as substrate binding.

The nucleic acid molecules also provide vectors for gene therapy in patients containing cells that are aberrant in enzyme gene expression. Thus, recombinant cells, which include the patient's cells that have been engineered ex vivo and returned to the patient, are introduced into an individual where the cells produce the desired enzyme protein to treat the individual.

The invention also encompasses kits for detecting the presence of a enzyme nucleic acid in a biological sample. Experimental data as provided in FIG. 1 indicates that the enzymes of the present invention are expressed in humans in the brain, kidney, colon, uterus detected by a virtual northern blot. For example, the kit can comprise reagents such as a labeled or labelable nucleic acid or agent capable of detecting enzyme nucleic acid in a biological sample; means for determining the amount of enzyme nucleic acid in the sample; and means for comparing the amount of enzyme nucleic acid in the sample with a standard. The compound or agent can be packaged in a suitable container. The kit can further comprise instructions for using the kit to detect enzyme protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the enzyme proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the enzyme gene of the present invention. FIG. 3 provides information on SNPs that have been found in the gene encoding the enzyme of the present invention. SNPs were identified at 4 different nucleotide positions in exon, introns and regions 5' and 3' of the ORF. Such SNPs in introns and outside the ORF may affect control/regulatory elements. Changes in the amino acid sequence caused by these SNPs is indicated in FIG. 3 and can readily be determined using the universal genetic code and the protein sequence provided in FIG. 2 as a reference.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified enzyme gene of the present invention can be routinely identified using the sequence information disclosed herein can be readily incorporated into one of the established kit formats which are well known in the art, particularly expression arrays.

Vectors/host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual*. 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroenzyme. Typical fusion expression vectors include pGEX (Smith et al, *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res*. 20:2111–2118 (1992)).

The nucleic acid molecules can also be expressed by expression vectors that are operative in yeast. Examples of vectors for expression in yeast e.g., S. cerevisiae include pYepSec1 (Baldari, et al., *EMBO J*. 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol*. 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J*. 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual*. 2nd, ed, Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual*. 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as enzymes, appropriate secretion signals are incorporated into the vector. The signal sequence can be endogenous to the peptides or heterologous to these peptides.

Where the peptide is not secreted into the medium, which is typically the case with enzymes, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a enzyme protein or peptide that can be further purified to produce desired amounts of enzyme protein or fragments. Thus, host cells containing expression vectors are useful for peptide production.

Host cells are also useful for conducting cell-based assays involving the enzyme protein or enzyme protein fragments, such as those described above as well as other formats known in the art. Thus, a recombinant host cell expressing a native enzyme protein is useful for assaying compounds that stimulate or inhibit enzyme protein function.

Host cells are also useful for identifying enzyme protein mutants in which these functions are affected. If the mutants naturally occur and give rise to a pathology, host cells containing the mutations are useful to assay compounds that have a desired effect on the mutant enzyme protein (for example, stimulating or inhibiting function) which may not be indicated by their effect on the native enzyme protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a enzyme protein and identifying and evaluating modulators of enzyme protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the enzyme protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the enzyme protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of S. cerevisiae (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, enzyme protein activation, and signal transduction, may not be evident from in vitro cell-free or cell-based assays. Accordingly, it is useful to provide non-human transgenic animals to assay in vivo enzyme protein function, including substrate interaction, the effect of specific mutant enzyme proteins on enzyme protein function and substrate interaction, and the effect of chimeric enzyme proteins. It is also possible to assess the effect of null mutations, that is, mutations that substantially or completely eliminate one or more enzyme protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
   (a) a nucleotide sequence that encodes a polypeptide having the amino acid sequence shown in SEQ ID NO:2 with 3B-hydroxy-5-C27-steroid oxido reductase activity;
   (b) a nucleic acid molecule consisting of the nucleic acid sequence of SEQ ID No: 1;
   (c) a nucleic acid molecule consisting of the nucleic acid sequence of SEQ ID No: 3; and
   (d) a nucleotide sequence that is completely complementary to a nucleotide sequence of (a)–(c).

2. A nucleic acid vector comprising a nucleic acid molecule of claim 1.

3. A host cell containing the vector of claim 2.

4. A method for detecting the presence of a nucleic acid molecule of claim 1 in a sample, said method comprising
   contacting the sample with an oligonucleotide comprising at least 20 contiguous nucleotides that hybridizes to said nucleic acid molecule under stringent conditions, wherein the stringent condition is hybridization in 6× sodium chloride/sodium citrate (SSC) at about 45° C., followed by one or more washes in 0.2×SCC, 0.1% SDS at 50–65° C., and
   determining whether the oligonucleotide binds to said nucleic acid molecule in the sample.

5. A process for producing a polypeptide comprising culturing the host cell of claim 3 under conditions sufficient for the production of said polypeptide, and recovering the peptide from the host cell culture.

6. An isolated polynucleotide consisting of a nucleotide sequence set forth in SEQ ID NO:1.

7. An isolated polynucleotide consisting of a nucleotide sequence set forth in SEQ ID NO:3.

8. A vector according to claim 2, wherein said vector is selected from the group consisting of a plasmid, virus, and bacteriophage.

9. A vector according to claim 2, wherein said isolated nucleic acid molecule is inserted into said vector in proper orientation and correct reading frame such that the protein of SEQ ID NO: 2 may be expressed by a cell transformed with said vector.

10. A vector according to claim 9, wherein said isolated nucleic acid molecule is operatively linked to a promoter sequence.

* * * * *